United States Patent
Vesterager

[11] Patent Number: 5,976,372
[45] Date of Patent: Nov. 2, 1999

[54] METHOD OF TREATING A BIOMASS IN ORDER TO REMOVE HEAVY METALS WITH HYDROGEN SULPHIDE

[76] Inventor: Niels Ole Vesterager, Poststrasse 4, Kropp, Germany, D-24848

[21] Appl. No.: 08/892,661

[22] PCT Filed: Jan. 15, 1996

[86] PCT No.: PCT/DK96/00024

§ 371 Date: Jul. 14, 1997

§ 102(e) Date: Jul. 14, 1997

[87] PCT Pub. No.: WO96/21625

PCT Pub. Date: Jul. 18, 1996

[30] Foreign Application Priority Data

Jan. 14, 1995 [DK] Denmark .................................. 0038/95

[51] Int. Cl.[6] .................................. C02F 1/52; C02F 3/28
[52] U.S. Cl. ........................ 210/603; 210/631; 210/717; 210/724; 210/912
[58] Field of Search .................................. 210/603, 607, 210/631, 717, 723, 724, 903, 906, 912

[56] References Cited

U.S. PATENT DOCUMENTS

| | | | |
|---|---|---|---|
| 4,354,937 | 10/1982 | Hallberg | 210/607 |
| 4,416,779 | 11/1983 | Ripl et al. | 210/631 |
| 4,758,344 | 7/1988 | Wildenauer | 210/603 |
| 4,839,052 | 6/1989 | Maree | 210/603 |
| 5,009,786 | 4/1991 | Oremland | 210/912 |
| 5,076,927 | 12/1991 | Hunter | 210/631 |
| 5,554,296 | 9/1996 | Suthersan | 210/717 |
| 5,587,079 | 12/1996 | Rowley et al. | 210/603 |

FOREIGN PATENT DOCUMENTS 9403403 2/1994 WIPO .

*Primary Examiner*—Christopher Upton
*Attorney, Agent, or Firm*—Watov & Kipnes, P.C.

[57] ABSTRACT

A method of treating a biomass comprising liquid manure from animal husbandry containing heavy metals, the method comprising the steps of subjecting the biomass to an anaerobic microbial degradation to form a biogas containing i.e. hydrogen sulphide gas, conveying at least a part of the biogas through at least a part of the microbially degraded biomass to precipitate the heavy metals as metal sulphides and separating the resulting mixture in a precipitate and a supernatant.

11 Claims, 4 Drawing Sheets

METHOD OF TREATING A BIOMASS IN ORDER TO REMOVE HEAVY METALS WITH HYDROGEN SULPHIDE

The present invention relates to a method of treating a biomass comprising liquid manure from animal husbandry containing heavy metals.

Liquid manure is a waste product from animal husbandry, which is rich in urea, organic matter, carbohydrates, fats, fibers, e.g. cellulose fibers, proteins, nutrient salts, and which also contains a certain amount of heavy metals. Liquid manure is widely used as a fertilizer for agricultural areas.

WO 94/03403 discloses a method of removing heavy metals from sludges, especially sewage sludges, 1) wherein the sludge is treated with sulphuric acid to solubilize the heavy metals, 2) wherein the resulting mixture is separated in a solid fraction and an aqueous fraction, 3) wherein the aqueous fraction is treated with hydrogen sulphide gas to precipitate heavy metal sulphides, 4) wherein the heavy metal sulphides are separated off and removed, and 5) wherein the aqueous fractions of step 2) and 4) are biologically reduced to convert sulphate into hydrogen sulphide.

EP-A1-80,981 discloses a method of treating sewage-water or raw-water so as to produce an aqueous concentrated solution of phosphorus and so as to recover heavy metal compounds, 1) wherein the water to be treated is subjected to a microbial aerobic purifying step in which the biological material is further separated by precipitation, 2) wherein the separated aqueous phase is subjected to a chemical treatment step in which iron is added to precipitate phosphorus, and in which a fraction containing solid matter including a major part of the iron and the heavy metals is separated, 3) wherein the separated solid matter fraction is treated with hydrogen sulphide under anaerobic conditions to form metal sulphides thus dissolving metal-bound phosphorus, the hydrogen sulphide being generated from biological decomposition of the biological material separated off in step 1), 4) wherein the metal sulphide fraction is separated from the aqueous phosphorus-containing fraction, and 5) wherein metal sulphide fraction is treated with e.g. a strong acid to form metal salts and hydrogen sulphide, the metal salts subsequently being recovered.

As a result of the use of liquid manure for fertilizing agricultural areas as mentioned above, the heavy metals of the liquid manure are introduced into the environment and thus into the food chain, which is highly undesirable due to the high toxicity of the heavy metals.

The problem of disposal also relates to a number of other heavy metal containing waste materials, such as organic waste materials from households and industry and sludge from waste water purification plants as well as ashes from the incineration thereof.

Waste materials having a relatively high content of heavy metals are often disposed of by deposition at a deposition site. Such a disposal is expensive and unsatisfactory from an environmental point of view, since it does not solve the problem, it just postphones it.

Waste materials having a relatively low content of heavy metals, such as sludge from waste water purification plants, are often disposed of by distribution on agricultural areas. This procedure means that heavy metals are introduced into the environment, which is undesirable for the same reasons as explained above in connection with the use of liquid manure for manuring purposes.

In recent years there has been an increasing focus on the issue of whether distribution of sludge from waste water purification plants on agricultural areas should be allowed, and in some countries such a practise is not used.

The object of the invention is to provide a method of the type stated in the preamble of claim 1, which is simple and does not require complicated process plants.

A further object of the invention is to provide a method, which utilizes the hydrogen sulphide gas formed in the microbial degradation of liquid manure, which hydrogen sulphide gas is undesirable due to its toxicity, and which may only be emitted to the atmosphere in very low amounts.

Also, hydrogen sulphide is undesirable due to its extremely high corrosive effect on process equipment, such as piping, reactor, valves, pumps, motors etc.

Yet a further object of the invention is to provide a method, which without the addition of precipitation agents has such a high potential for removing heavy metals that in addition to the liquid manure other materials containing heavy metals may be purified.

This object is achieved with the method of the invention, which method is characterized in subjecting the biomass to an anaerobic microbial degradation to form a biogas containing i.a. hydrogen sulphide gas, conveying at least a part of the biogas through at least a part of the microbially degraded biomass to precipitate the heavy metals as metal sulphides, and separating the resulting mixture in a precipitate and a supernatant.

The invention is based on the discovery that microbial degradation of liquid manure yields a very high amount of hydrogen sulphide gas, and that the said amount is high enough to precipitate not only the heavy metals of the liquid manure itself but also a considerable amount of heavy metals from other materials.

Thus, the amount of hydrogen sulphide gas formed in the microbial degradation of liquid manure is many times higher than that of e.g. waste water sludge. In fact the amount of hydrogen sulphide gas formed in the microbial degradation of sludge is not even sufficient to precipitate the heavy metal content of the sludge itself.

Furthermore, the invention is based on the recognition that when liquid manure is used as a biomass source in a biogas production process, it is highly advantageous to combine the biogas production process with a waste water purification process, since such a combination makes it possible to remove all implicated undesirable substances, i.e. both the heavy metals present in the biomass source as well as in the waste water sludge, and the hydrogen sulphide generated in the biogas production process.

Also, the liquid manure yields an amount of methane gas corresponding to an amount of power, which is sufficient not only to run an entire plant of liquid manure and sludge processing, but which also leaves an excess amount, which may be put into a connected power distribution net.

A first preferred embodiment of the method of the invention is characterized in separating the microbially degraded biomass in a solid fraction and a liquid fraction and conveying the said biogas through the said liquid fraction.

The separation of the microbially degraded biomass may e.g. be carried out by centrifugation or by use of a press, e.g. a worm extruder, a filter press or a sieve belt press.

When the microbially degraded biomass is separated in a solid fraction and in a liquid fraction, the solid fraction is preferably incinerated to form ashes, which is supplied to the liquid fraction to be treated with the biogas.

The incineration of the solid fraction has the advantage that the heavy metals are concentrated strongly and that the heavy metals, which are bonded to the solid matter, are released into free form so as to make them readily available for precipitation with sulphide.

A second preferred embodiment of the method of the invention is characterized in that in addition to the liquid manure the biomass comprises an organic waste material, such as an organic waste material from households and industry, sludge from water purification plants and mixtures thereof.

A third preferred embodiment of the method of the invention is characterized in using a waste water sludge containing heavy metals and conveying a part of the said biogas through the sludge to precipitate the heavy metals as metal sulphides.

In the said third preferred embodiment the treatment of the biomass with biogas and the treatment of the sludge with biogas are preferably conducted in separate operations.

The sludge used is preferably dewatered sludge, which is suspended in the lowest possible amount of water so as to extract those heavy metals of the sludge, which is not biologically bound in the organic matter.

Such an extraction may remove up to about 90% of the heavy metal content of the sludge.

Subsequent to the extraction the sludge is separated from the liquid e.g. by centrifugation or by use of a press, e.g. a worm extruder, a filter press or a sieve belt press.

If the content of the remaining heavy metals is acceptable, the separated sludge may be discharged and used, e.g. for fertilizing agricultural fields. Otherwise, the separated sludge may be transferred to the step of microbial degradation.

It is desirable to remove the major part of the heavy metals from the sludge before introducing it into the step of microbial degradation, since the heavy metals are toxic to the microorganisms and thus have an impairing effect on biogas production rate and efficiency.

When conducting the method of the invention in accordance with the above first and third preferred embodiment, the solid fraction of the biomass is preferably incinerated to form ashes, which are supplied to the sludge to be treated with the biogas.

The ashes contain heavy metals in a relatively concentrated form, and in order to obtain the best possible control of the precipitation of heavy metal sulphides, it is expedient to add the ashes to the smallest volume possible, and the volume of the sludge is usually smaller than the volume of the biomass.

In addition to the ashes obtained in the incineration of the solid fraction of the microbially degraded biomass or as an alternative thereto ashes containing heavy metals obtained from other sources than the said biomass may be added to the biomass and/or sludge to be treated with the biogas.

The biogas formed in the anaerobic microbial degradation of the biomass contains methane, carbondioxide, ammonia and hydrogen sulphilde, the ratio of which depends on the type and composition of the biomass.

When the biomass and the sludge are being treated in separate operations the biogas from the microbial degradation of the biomass may be supplied to the said two operations sequentially or it may be divided into two flows.

According to a fourth preferred embodiment of the method of the invention, the pH-value of the biomass and/or the sludge to be treated with the biogas is adjusted to a number of different levels of from about 0 to 9 so as to precipitate the heavy metals substantially selectively.

The fourth embodiment of the invention is based on the discovery that different heavy metals precipitate as sulphides at different pH-levels, and that this fact may be used to obtain precipitation products in the form of pure or substantially pure metal sulphides, which are suitable for reuse, and which do not need to be disposed of by deposition.

The selective precipitation of the various heavy metals is preferably carried out by lowering the pH of the precipitation liquid to a level at which none of the heavy metals precipitate, e.g. pH equal to 0, and then raising the pH value stepwise to the levels at which precipitation of the different heavy metals take place, which levels depend on the concentration of sulphide and the heavy metal in question.

The acid used to adjust the pH-level may be hydrocloric acid, phosphoric acid and sulphuric acid, preferably hydrochloric acid.

The base used to adjust the pH-level may be sodium hydroxide or potassium hydroxide.

The precipitated heavy metal sulphides may be separated from the liquid by centrifugation or by use of a press, e.g. a worm extruder, a filter press or a sieve belt press.

In connection with the present invention the term "heavy metals" includes the following metals: Cadmium, mercury, copper, zink, lead, nickel, tin, arsenic, molybdenum, cobalt and manganese.

The addition of additional materials containing heavy metals is preferably controlled in such a manner that the biogas after passage of the microbially degraded biomass, and sludge and ashes, if any, is free of or substantially free of hydrogen sulphide.

Carbon dioxide and ammonia are preferably separated off the remaining biogas and the resulting methane gas may then be used as a fuel and transformed into heat and/or electricity.

A fifth preferred embodiment of the method of the invention is characterized in processing the supernatant so as to reduce the content of substances containing nitrogen and phosphorus, such as nitrate, ammonium and phosphate.

The nitrogen and phosphorus removed from the supernatant are preferably converted into solid compounds, which are suitable as a fertilizer. The said conversion is preferably conducted in accordance with the process described in WO 92/08674, the disclosure of which is included herein by this reference.

When the method of the invention comprises such a fertilizer producing process, it is possible to put the starting biomass through a step of the said process to remove the major part of its nitrogen containing compounds before supplying the biomass to the microbial degradation step. By such a pre-treatment of the biomass, the amount of ammonia formed in the microbial degradation step is reduced, such a reduction being desirable, since ammonia has an impairing effect on the biogas production rate and efficiency.

In connection with the present invention the expressions "liquid manure" and "liquid manure from animal husbandry" means a mixture of faeces and urine from animals or a slurry of faeces in a suitable liquid, such as water.

In the following the invention will be described in further detail with reference to the drawings, wherein FIG. 1 shows a general flow diagram of a preferred embodiment of the invention in the form of a total process for treating organic waste, liquid manure and sludge.

Figure 1:
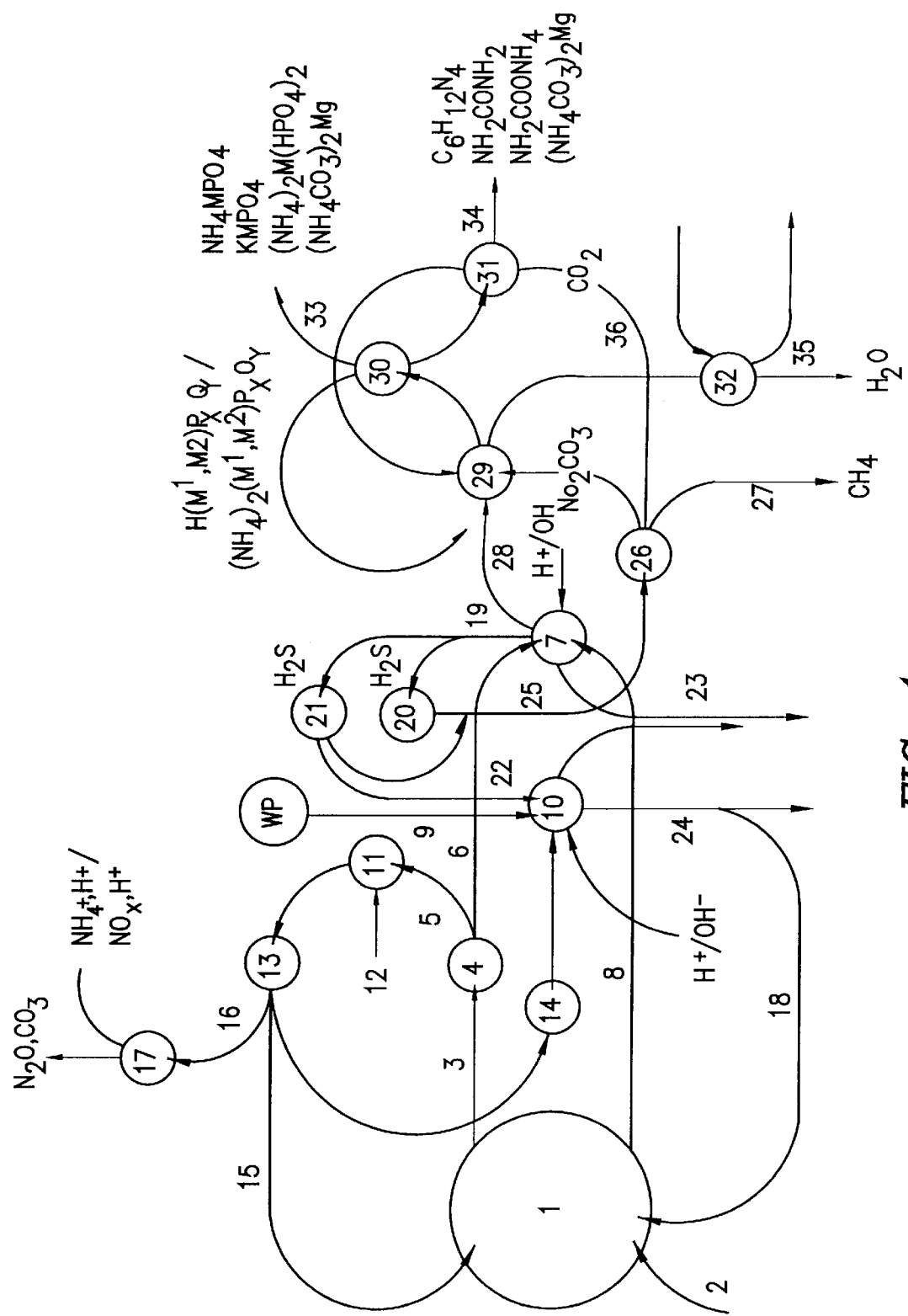
FIG. 1 shows a plant comprising a biogas reactor 1, to which a biomass 2 comprising liquid manure and obtionally organic waste material is supplied.

The microbially degraded biomass 3 is transferred to a separator 4, wherein the biomass 3 is separated in a solid fraction 5 and in a liquid fraction 6. The liquid fraction 6 is transferred to a first precipitation step 7, and the biogas 8 discharged from the reactor 1 is conveyed through the liquid in the step 7 to precipitate the heavy metals therein as metal sulphides.

Dewatered sludge 9 from a waste water purification plant WP is supplied to a second precipitation step 10.

The solid fraction 5, which may be pelleted in a pelleting apparatus 11, to which additional biomass 12 may be added, is transferred to a furnace 13, wherein it is incinerated to form ashes 14, which are then transferred to the step 10 in order to precipitate the heavy metals contained in the ashes 14 as metal sulphides. Also, the ashes contain a considerable amount of compounds containing nitrogen and phosphorus, which is re-introduced into the process in order to convert the said compounds into useful fertilizing compounds, see below.

The heat 15 of combustion evolved in the furnace 11 may be used to heat the biogas reactor 1. The flue gas 16 from the furnace 11 may be purified in a washing tower 17. In the washing of the flue gas 16, hydrochloric acid is formed, which hydrochloric acid may be used to adjust the pH-value in the precipitation steps 7 and 10 or elsewhere in the process.

In step 10 the heavy metals of the sludge are extracted therefrom with water, and the resulting mixture is separated in a solid fraction 18, which is recycled to the biogas reactor 1, and a liquid fraction, from which the heavy metals are precipitated with hydrogen sulphide.

After passage of the precipitation step 7 a part of the hydrogen sulphide has been removed from the biogas 19. The biogas 19 is then alternately transferred to two storage tanks 20 and 21, wherein the biogas 19 is reacted with iron to form iron sulphide in which form the sulphide is stored in the tanks 20 and 21.

Depending on the requirement for hydrogen sulphide gas in the second precipitation step 10, iron sulphide taken alternately from the two tanks 20 and 21 is converted back into hydrogen sulphide 22 by addition of acid, and the reformed hydrogen sulphide 22 is transferred to the step 10 to precipitate the heavy metals present therein.

The storage tanks 20 and 21 allow hydrogen sulphide to be stored in periods where more hydrogen sulphide than is needed in the precipitation steps 7 and 10 is formed in the biogas reactor 1, and conversely the storage tanks 20 and 21 serve as a reservoir of sulphide in periods where less hydrogen sulphide than needed is generated in reactor 1.

As an alternative or supplement to storing sulphide in the form of iron sulphide, sulphide may be stored in the form of heavy metal sulphide, e.g. copper sulphide, formed in the method of the invention. Storage of sulphide as heavy metal sulphide provides a possibility of converting the heavy metal sulphide to a different compound, e.g. heavy metal chloride by addition of hydrochloric acid, if desired.

The amounts of ashes 14 and sludge 9 supplied to the precipitation step 10 are adjusted to the amount of hydrogen sulphide supplied to the step 10 from one of the storage tanks 20 or 21.

The heavy metal sulphides formed in the precipitation steps 7 and 10 are separated off and removed from the process (flows 23 and 24, respectively).

After passage of one of the storage tanks 20 and 21, all or substantially all of the hydrogen sulphide has been removed from the biogas 25.

In step 26, carbon dioxide is removed from the biogas 25. Carbon dioxide is removed by contacting the biogas 25 with an aqueous solution of ammonium and e.g. sodium chloride to effect the following reactions:

$$CO_2 + NH_4^+ \rightarrow NH_4HCO_3 \qquad (1)$$

$$NH_4HCO_3 + NaCl \rightarrow NaHCO_3 + NH_4Cl \qquad (2)$$

Subsequently, the reaction products of reaction (2) are reacted as follows:

$$2\ NaHCO_3 \xrightarrow{heat} Na_2CO_3 + H_2O + CO_2 \qquad (3)$$

$$NH_4Cl \xrightarrow{base} NH_3 + HCl \qquad (4)$$

MgCl may be used as an alternative to NaCl.

For a full account of the conversion of gaseous carbon dioxide to carbonate, reference is made to EP-A1-0.628.339, the disclosure of which is included herein by this reference.

The resulting biogas 27 consisting almost exclusively of methane is removed from the process and used as a fuel.

The supernatant from the precipitation in step 10 is recycled to the biogas reactor 1 together with the solid fraction 18.

The supernatant 28 from the precipiation in step 7 is transferred to a step 29, 30, 31, 32, wherein compounds containing nitrogen and phosphorus are converted into compounds 33, 34, which are suitable as fertilizers. Purified water 35 is then discharged from the process.

The carbon dioxide 36 formed in reaction (3) in step 26 may be transferred to the step 31.

For a full account of step 29, 30, 31, 32, reference is made to WO 92/08674.

Figure 2:
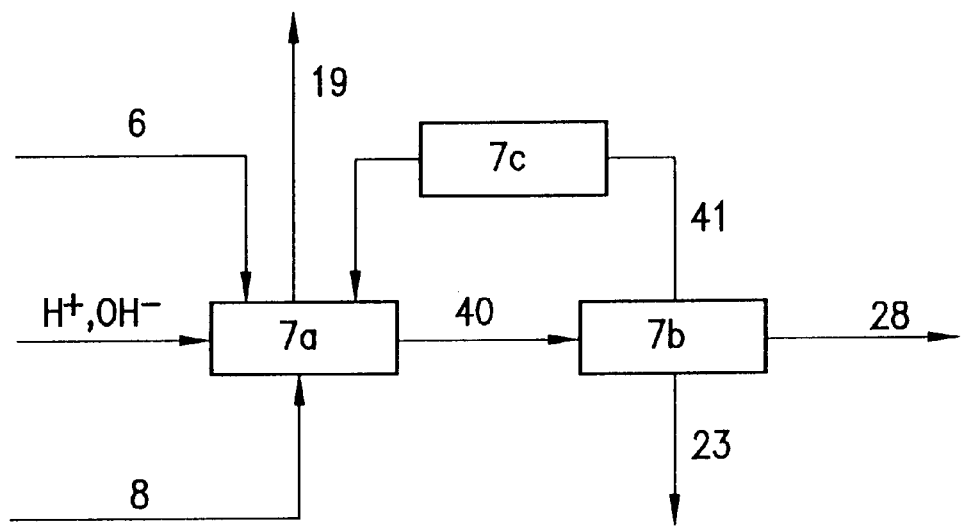
FIG. 2 shows a more detailed flow diagram of step 7 in FIG. 1.

FIG. 2 shows a precipitation tank 7a, a centrifuge 7b and a collecting tank 7c. The liquid fraction 6 of the biomass is supplied to tank 7a, and the pH-value of the tank 7a may then be adjusted to a desired level by addition of acid or base, e.g. a pH-level, where one specific heavy metal may be precipitated with hydrogen sulphide 8.

The resulting mixture 40 of precipitate and supernatant is then transferred to the centrifuge 7b, wherein the mixture 40 is separated in a precipitate 23 and a supernatant 41, which is collected in the tank 7c and subsequently recycled to the tank 7a for precipitation of another heavy metal. This procedure is repeated until all types of heavy metals have been selectively precipitated and separated off, and then the resulting supernatant 28 free of heavy metals may be discharged from the step 7.

Figure 3:
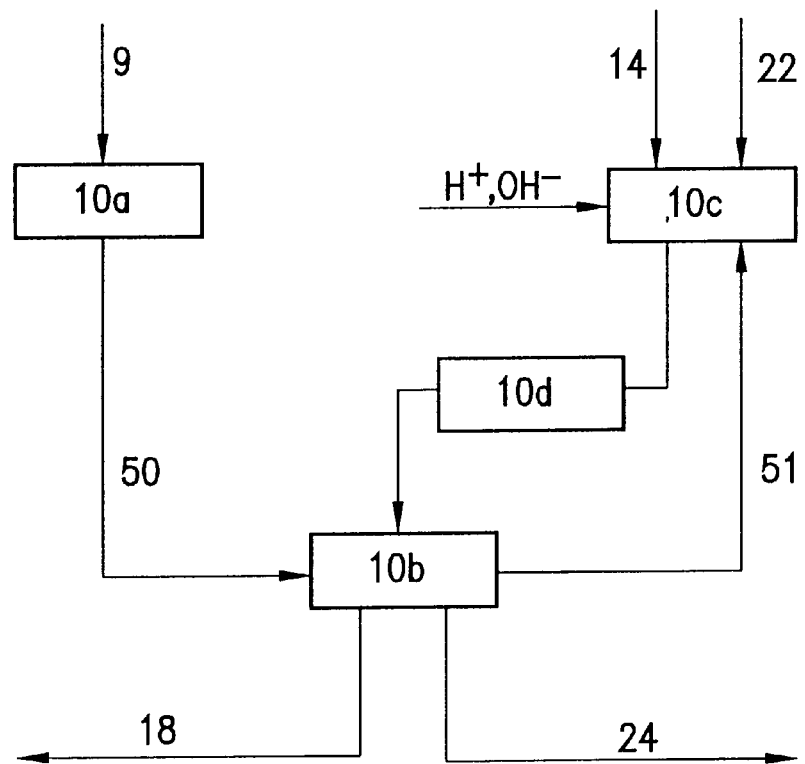
FIG. 3 shows a more detailed flow diagram of step 10 in FIG. 1.
Figure 4:
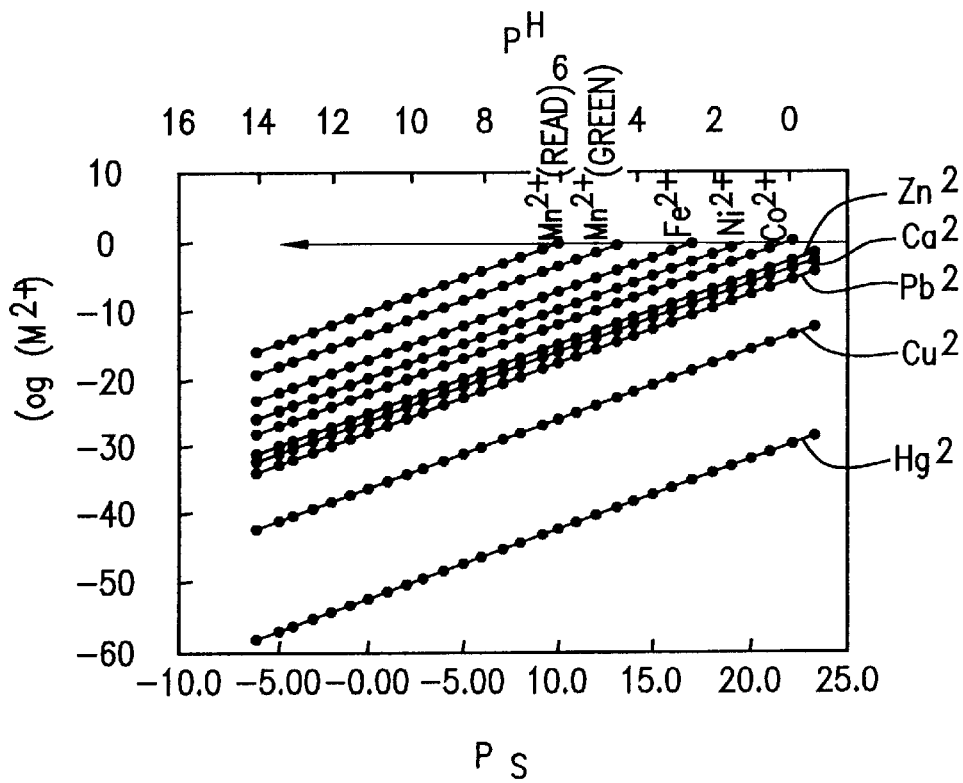
FIG. 4–6 show diagrams of the pH-value at which various heavy metals precipitate as a function of the concentration of the heavy metal and as a function of the concentration of sulphide, hydroxide and carbonate, respectively.
Figure 5:
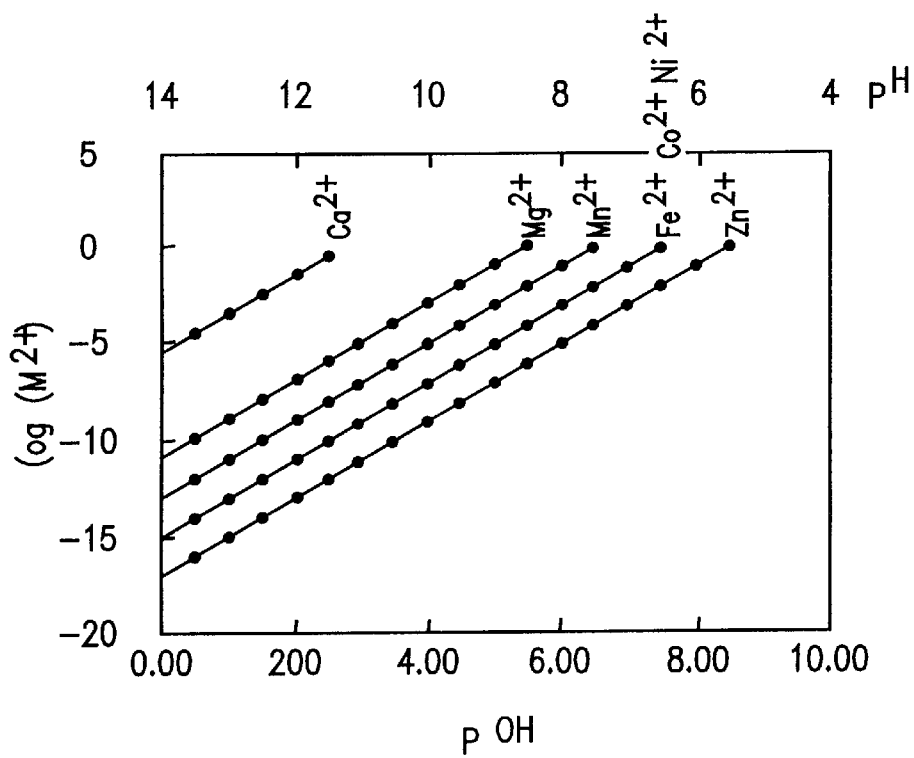
Figure 6:
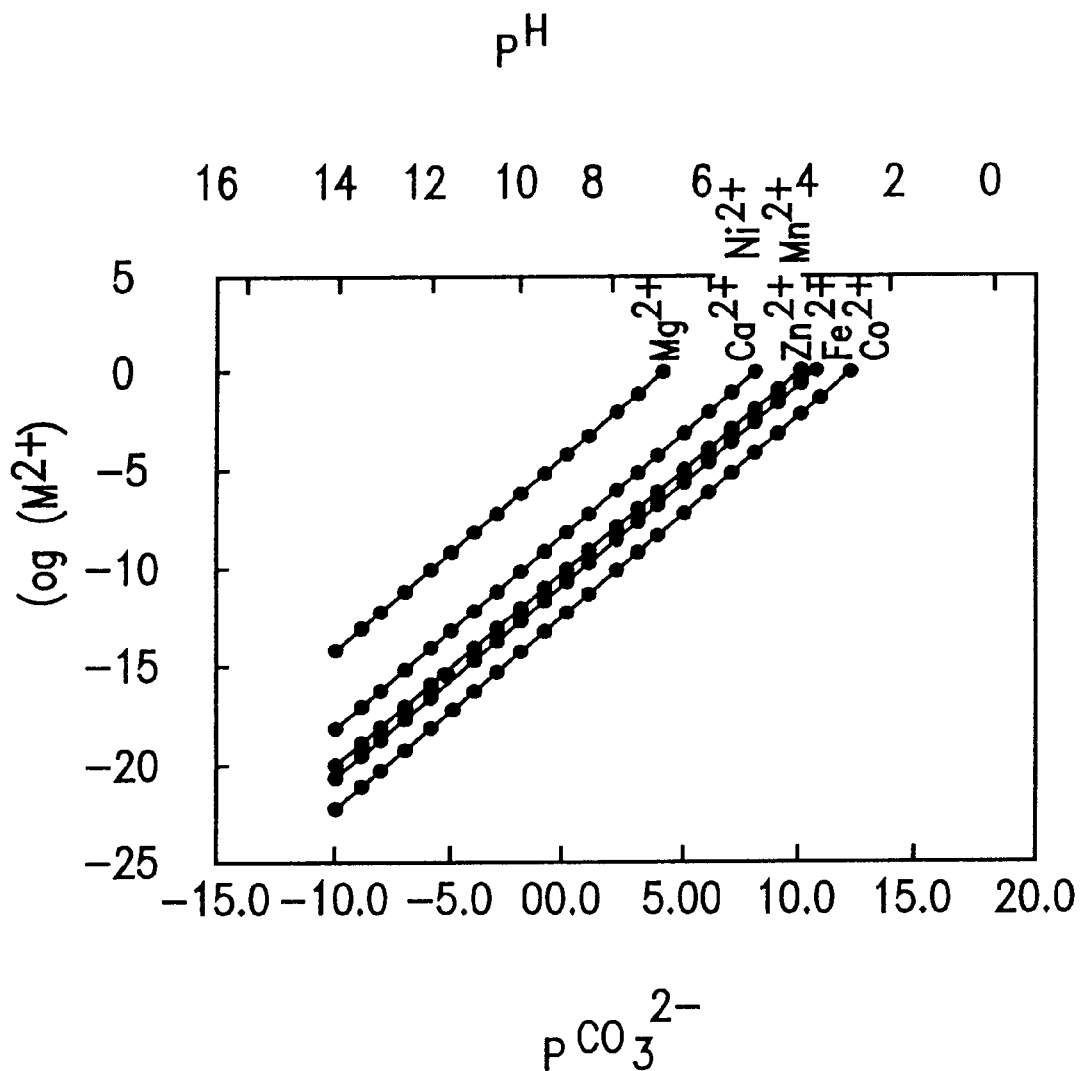

FIG. 3 shows an extraction tank 10a, a centrifuge 10b, a precipitation tank 10c and a collecting tank 10d. Dewatered sludge 9 is supplied to the tank 10a, where the sludge 9 is suspended in the smallest possible amount of water to extract the heavy metals from the sludge. The resulting mixture 50 of water and sludge is transferred to the centrifuge 10b, wherein the mixture 50 is separated in a solid fraction 18 and an aqueous fraction 51, the latter being transferred to the precipitation tank 10c. Selective precipitation of different heavy metals is then carried using the procedure disclosed above.

The tank 10c contains a liquid phase and above this a gaseous phase, and the tank 10c is equipped with a gas outlet. The content of hydrogen sulphide in the gaseous phase is measured continuously, and if the content is above a certain very low set point, the gas outlet is closed, and additional sludge 9 and/or ashes 14, i.e. additional heavy metal loading, is supplied to the step 10 to remove the excess of hydrogen sulphide in tank 10c.

The invention will now be described in further detail with reference to the following examples.

EXAMPLE 1

10 liters of a biomass consisting of a mixture of 80% by volume of liquid manure and 20% by volume of organic industrial waste material was fed continuously into a bioreactor having a volume of 15 liters, wherein biogas is produced. The microbially degraded biomass, which is discharged continuously from the bioreactor is collected and transferred to a centrifuge, wherein the biomass is separated in a solid fraction and a liquid fraction.

The separated solid fraction is removed and composted. The liquid fraction is transferred to a precipitation tank, and hydrochloric acid is added to adjust the pH-value to 8.1, and then the biogas is bubbled through the liquid fraction to precipitate the heavy metals present therein, viz. copper and zinc ions.

Table 1 gives the content of $Cu^{2+}$ and $Zn^{2+}$ in the liquid fraction before and after treatment with the biogas and the composition of the biogas before and after passage of the liquid fraction.

TABLE 1

| | | Before the biogas passes through the liquid fraction | After the biogas has passed through the liquid fraction |
|---|---|---|---|
| Content of heavy metal ion in liquid fraction [mg/kg solids of biomass] | $Cu^{2+}$ | 1200 | 0.00 |
| | $Zn^{2+}$ | 248 | 0.05 |
| Content of component in biogas [% by volume] | $CH_4$ | 68.6 | 68.9 |
| | $CO_2$ | 31.0 | 31.1 |
| | $H_2S$ | 0.3 | 0.0340 |
| | Balance | 0.1 | 0.0003 |

The precipitate contained about 82.9% by weight of CuS and about 17.1% by weight of ZnS.

To reduce the content of hydrogen sulphide in the biogas further, process ashes from an external biomass incineration containing heavy metals is dissolved in a solution, and the pH-value is adjusted with acid to 10.0, and the biogas discharged from the liquid fraction of the biomass is then bubbled through the said solution.

TABLE 2

| | | After the biogas has passed through the liquid fraction and the solution of ashes |
|---|---|---|
| Content of component in biogas [% by volume] | $CH_4$ | 68.9 |
| | $CO_2$ | 31.1 |
| | $H_2S$ | 0.0002 |
| | Balance | 0.0003 |

EXAMPLE 2

A biomass consisting of 75% of liquid manure, 15% waste water sludge and 10% industrial organic waste material by volume was microbially degraded in a continuous bioreactor having a volume of 15 liters to produce biogas. The microbially degraded biomass was separated in a liquid and a solid fraction in a centrifuge. The solid fraction is dried and incinerated, and the liquid fraction is transferred to a precipitation tank, the pH-value is adjusted to 8.1 with phosphoric acid, and the biogas is bubbled through the liquid phase to precipitate the heavy metals therein.

Table 3 gives the content of heavy metals in the liquid fraction before and after treatment with the biogas and the composition of the biogas before and after passage of the liquid fraction.

TABLE 3

| | | Before the biogas passes through the liquid fraction | After the biogas has passed through the liquid fraction |
|---|---|---|---|
| Content of heavy metal ion in liquid fraction [mg/kg solids of biomass] | $Cu^{2+}$ | 2250 | 0.000 |
| | $Pb^{2+}$ | 352 | 0.01 |
| | $Zn^{2+}$, $Sn^{2+}$ | Traces | — |
| Content of component in biogas [% by volume] | $CH_4$ | 68.6 | 68.9 |
| | $CO_2$ | 31.0 | 31.1 |
| | $H_2S$ | 0.3 | 0.0002 |
| | Balance | 0.1 | 0.0003 |

The precipitate of heavy metals is separated from the liquid phase by centrifugation using a flocculating agent.

The composition of the precipitate was analyzed, and it contained about 86.5% CuS, about 12.5% PbS and about 1.0% ZnS and SnS by weight.

EXAMPLE 3

An experiment corresponding to that of Example 2 was carried out with the modifications that the biomass consisted of 90% liquid manure and 10% industrial organic waste material by volume and that the pH-value of the liquid fraction was adjusted with acid to 5.0 to precipitate $Cu^{2+}$ and $Zn^{2+}$ as sulphides and then to 8.5 with NaOH to precipitate $Mg^{2+}$ and $Mn^{2+}$ as hydroxides, after which $CO_3^{2-}$ was added to precipitate $Ca^{2+}$ as carbonate.

Table 4 gives the results obtained.

TABLE 4

| | | Before the biogas passes through the liquid fraction | After the biogas has passed through the liquid fraction |
|---|---|---|---|
| Content of (heavy) metal ion in liquid fraction [g/m³] | $Cu^{2+}$ | 20 | 2 |
| | $Mg^{2+}$ | 34 | 13 |
| | $Ca^{2+}$ | 1200 | 135 |
| | $Zn^{2+}$ | 19 | 8 |
| | $Mn^{2+}$ | 17 | 7 |
| Content of component in biogas [% by volume] | $CH_4$ | 63.6 | 71.7 |
| | $CO_2$ | 36.0 | 28.3 |
| | $H_2S$ | 0.3 | 0.0002 |
| | Balance | 0.1 | 0.0003 |

I claim:

1. A method of treating a biomass comprising liquid manure from animal husbandry containing heavy metals, comprising subjecting the biomass to an anaerobic microbial degradation to form a biogas containing hydrogen sulphide gas and a microbially degraded biomass separating the microbially degraded biomass into a solid fraction and a liquid fraction, conveying at least a part of the biogas through at least a part of the liquid fraction to precipitate the heavy metals as metal sulphides, and separating the resulting mixture into a precipitate and a supernatant.

2. A method according to claim 1, further comprising incinerating the said solid fraction to form ashes and supplying the ashes thus formed to the said liquid fraction to be treated with the biogas.

3. A method according to claim 1, wherein the biomass further comprises an organic waste material.

4. A method according to claim 1, further comprising conveying a part of said biogas through a waste water sludge containing heavy metals to precipitate the heavy metals as metal sulphides.

5. A method according to claim 4, comprising conducting the treatment of the biomass with the biogas and the treatment of the sludge with the biogas in separate operations.

6. A method according to claim 5, comprising incinerating the solid fraction of the biomass to form ashes and supplying the ashes thus formed to the said sludge to be treated with the biogas.

7. A method according to claim 5, comprising supplying an incineration ash containing heavy metals to the biomass, the sludge or a mixture thereof to be treated with the biogas.

8. A method according to claim 7, comprising adding additional materials containing heavy metals under controlled conditions in such a manner that the biogas after passage of the microbially degraded biomass, and sludge and ashes, if any, is free of or substantially free of hydrogen sulphide.

9. A method according to claim 5, comprising adjusting the pH-value of the biomass, the sludge or a mixture thereof to be treated with the biogas to a plurality of different levels of from about 0 to 9 so as to precipitate the heavy metals substantially selectively.

10. A method according to claim 1, comprising processing the supernatant so as to reduce the content of nitrogen and phosphorus.

11. A method according to claim 10, further comprising converting the nitrogen and phosphorus removed from the supernatant into solid compounds, which are suitable as a fertilizer.

* * * * *